United States Patent
Peoples et al.

(10) Patent No.: US 11,111,202 B2
(45) Date of Patent: Sep. 7, 2021

(54) PRODUCTION OF SALTS OF 4-HYDROXYBUTYRATE USING BIOBASED RAW MATERIALS

(71) Applicant: CJ Cheiljedang Corporation, Seoul (KR)

(72) Inventors: Oliver P. Peoples, Arlington, MA (US); Derek Samuelson, Somerville, MA (US); Max Senechal, Arlington, MA (US); Sung Min Park, Arlington, MA (US); Joseph Gredder, Cambridge, MA (US); Christopher Mirley, Winthrop, MA (US)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/241,217

(22) Filed: Jan. 7, 2019

(65) Prior Publication Data
US 2019/0135729 A1 May 9, 2019

Related U.S. Application Data

(62) Division of application No. 14/442,413, filed as application No. PCT/US2013/065916 on Oct. 21, 2013, now abandoned.

(Continued)

(51) Int. Cl.
*A61K 9/28* (2006.01)
*C07C 59/01* (2006.01)
(Continued)

(52) U.S. Cl.
CPC ............... *C07C 59/01* (2013.01); *A61K 9/28* (2013.01); *A61K 47/34* (2013.01); *A61L 17/105* (2013.01);
(Continued)

(58) Field of Classification Search
CPC ......... A61K 47/34; A61K 9/28; A61L 17/105; C07C 51/41; C07C 59/01; C07D 307/06; C07D 307/33; C08G 63/06
See application file for complete search history.

(56) References Cited

U.S. PATENT DOCUMENTS 3,467,679 A   9/1969  Rogers
4,421,865 A   12/1983 Shen
(Continued)

FOREIGN PATENT DOCUMENTS

EP   2630137 A1   8/2013
WO   97-07216 A1  2/1997
(Continued)

OTHER PUBLICATIONS

Aguayo et al. (The Journal of Biological Chemistry 1988;263(36): 19552-19557). (Year: 1988).*
(Continued)

*Primary Examiner* — Ernst V Arnold
(74) *Attorney, Agent, or Firm* — Christensen, Fonder, Dardi; Diane E. Bennett; Peter S. Dardi

(57) ABSTRACT

Gamma-butyrolactone ("GBL") and Gamma-hydroxybutyrate ("GHB") having a unique carbon footprint as defined by the percent modern carbon (pmc) are described herein. The percent modern carbon can be controlled by varying the amounts of biobased, renewable starting materials and petroleum-based starting materials to prepare GBL or GHB having a defined pmc or by preparing mixtures of GBL or GHB prepared from biobased renewable starting materials and GBL or GHB prepared from petroleum-based starting materials.

6 Claims, 1 Drawing Sheet

Related U.S. Application Data

(60) Provisional application No. 61/834,974, filed on Jun. 14, 2013, provisional application No. 61/823,518, filed on May 15, 2013, provisional application No. 61/772,602, filed on Mar. 5, 2013, provisional application No. 61/726,294, filed on Nov. 14, 2012.

(51) Int. Cl.
| | | |
|---|---|---|
| *C07D 307/06* | (2006.01) | |
| *C07D 307/33* | (2006.01) | |
| *A61K 47/34* | (2017.01) | |
| *A61L 17/10* | (2006.01) | |
| *C07C 51/41* | (2006.01) | |
| *C08G 63/06* | (2006.01) | |

(52) U.S. Cl.
CPC ............ *C07C 51/41* (2013.01); *C07D 307/06* (2013.01); *C07D 307/33* (2013.01); *C08G 63/06* (2013.01)

(56) References Cited

U.S. PATENT DOCUMENTS

| | | | |
|---|---|---|---|
| 5,221,768 | A | 6/1993 | Kato et al. |
| 5,990,162 | A | 12/1999 | Schar |
| 6,245,537 | B1 | 6/2001 | Williams et al. |
| 6,316,262 | B1 | 11/2001 | Huisman et al. |
| 6,548,569 | B1 | 4/2003 | Williams et al. |
| 6,610,764 | B1 | 8/2003 | Martin et al. |
| 6,623,730 | B1 | 9/2003 | Williams et al. |
| 6,689,589 | B2 | 2/2004 | Huisman et al. |
| 6,780,889 | B2 | 8/2004 | Cook et al. |
| 7,081,357 | B2 | 7/2006 | Huisman et al. |
| 7,229,804 | B2 | 6/2007 | Huisman et al. |
| 7,262,219 | B2 | 8/2007 | Cook et al. |
| 7,572,605 | B2 | 8/2009 | Mamelak et al. |
| 7,576,173 | B2 | 8/2009 | van Walsem et al. |
| 7,851,506 | B2 | 12/2010 | Cook et al. |
| 7,981,642 | B2 | 7/2011 | van Walsem et al. |
| 8,034,270 | B2 | 10/2011 | Martin et al. |
| 8,203,021 | B2 | 6/2012 | Fruchey et al. |
| 8,246,792 | B2 | 8/2012 | Fruchey et al. |
| 8,263,650 | B2 | 9/2012 | Cook et al. |
| 8,461,191 | B2 | 6/2013 | Castro et al. |
| 8,461,197 | B2 | 6/2013 | Tung |
| 2006/0210630 | A1 | 9/2006 | Liang et al. |
| 2009/0075351 | A1 | 3/2009 | Burk et al. |
| 2010/0304453 | A1 | 12/2010 | Trawick et al. |
| 2011/0028551 | A1 | 2/2011 | Levin et al. |
| 2011/0111027 | A1 | 5/2011 | Rourke et al. |
| 2012/0076865 | A1 | 3/2012 | Allphin et al. |
| 2012/0122952 | A1 | 5/2012 | Tung |
| 2013/0207043 | A1 | 8/2013 | Menozzi et al. |

FOREIGN PATENT DOCUMENTS

| | | |
|---|---|---|
| WO | 99/09972 A1 | 3/1999 |
| WO | 00-38672 | 7/2000 |
| WO | 01-19361 A2 | 3/2001 |
| WO | 2009-059253 A2 | 5/2009 |
| WO | 2010-053691 A1 | 5/2010 |
| WO | 2010-092304 A1 | 8/2010 |
| WO | 2010-124046 A1 | 10/2010 |
| WO | 2011-100601 A1 | 8/2011 |
| WO | 2012-051473 A1 | 4/2012 |
| WO | 2012-142162 A2 | 10/2012 |
| WO | 2014-078014 A2 | 5/2014 |

OTHER PUBLICATIONS

Giri et al. (International Journal of Engineering Technology Science and Research 2018;5(3): 1706-1710). (Year: 2018).*
Gross et al. (Polymer Preprints 1989;30(2):398-9; Abstract 1 page). (Year: 1989).*
Basaki et al., "Anti-angiogenic activities of UFt and its metabolites, GHB and GBL, in the dorsal air sac (DAS) model in mice" Gan to Kagaku Ryoho. Cancer & Chemotherapy, 27:93-98 (2000). (Abstract Only).
Church et al, "Catalytic Air Oxidation of Crotonaldehyde to Maleic Anhydride", I&EC Product Research and Development, vol. 2 (1), p. 61-66, (1963). (Abstract Only).
Leonenkov et al., "Use of lithium oxybutyrate for improving results in the early post-operative period in lung cancer patients", Voprosy Onkologii, 39:75-79 (1993). (Abstract Only).
Müller et al., "A Novel Complex with Boat-Shaped, Synfacially Bound η3:η3-Benzene Bridges and the First η3-η2: η2:η2-Arenetrirhodium Complex†‡", Angew. Chem. Int. Ed. Engl., 32:447-503 (Dec. 1993). (Abstract Only).
Rowe et al., "Handbook of Pharmaceutical Excipients", Pharmaceutical Press, 4th Ed., (2003). (Abstract Only).
Sendelbeck et al., "Disposition of a 14C-labeled bioerodible polyorthoester and its hydrolysis products, 4-hydroxybutyrate and cis,trans-1,4-bis(hydroxymethyl)cyclohexane, in rats," Drug Metabolism & Disposition 13:291-295 (1985). (Abstract Only).
Scharf et al., "Pharmacokinetics of gammahydroxybutyrate (GHB) in narcoleptic patients", Sleep, 21(5):507-14 (Aug. 1, 1998). (Abstract Only).
Williams et al., "PHA applications: addressing the price performance issue: I. Tissue engineering.", Int. J. Biol. Macromol., 25: 111-21, (Jun.-Jul. 1999). (Abstract Only).
Yonekura et al., "UFT and its metabolites inhibit the angiogenesis induced by murine renal cell carcinoma, as determined by a dorsal air sac assay in mice", Clinical Cancer Research, 5:2185-91 (1999). (Abstract Only).
Office Action from co-pending European Patent Application No. 13802137.3 dated Feb. 13, 2018.
Deuterium [online] retrieved on Jan. 9, 2017 from https://www.britannica.com/print/article/159684; 2 pages.
Kasture (Pharmaceutics-I 2008 Pragati Books Pvt. Ltd. 1 page).
Marclay et al., "Potential of IRMS Technology for Tracing Gamma-butyrolactone (GBL)," Forensic Sci Int, 198(1-3): 46-52 (2010).
Marclay et al., "Source Inference of Exogenous Gamma-hydroxybutyric Acid (GHB) Adminstered to Humans by Means of Carbon Isotopic Ratio Analysis: Novel Perspectives Regarding Forensic Investigation and Intelligence Issues," Anal and Bioanal Chem, 400(4): 1105-1112 (2011).
Martin et al., (Biomedical Engineering Journal 2003; 16:97-105).
Otsuka et al., (Journal of Pharmaceutical Sciences 1995; 84(4): 443-447).
Petroleum—Oil and Natural Gas ([online] retrieved on Feb. 8, 2018 from: http://energy4me.org/all-about-energy/what-is-energy/energy-sources/petroleum/; 14 pages.
Remingtons Pharmaceutical Sciences 17th Ed. (1985); p. 1633.
Ritter ([online] retrieved from: https://pubs.acs.org/cen/news/89/i26/8926notw1e.html; Jun. 27, 2011; 5 pages.
Saudan et al., "Detection of Exogenous GHB in Blood by Gas Chromatography-Combustion-Isotope Ratio Mass Spectrometry: Implications in Postmortem Toxicology," Anal Toxicol, 29(8): 777-781 (2005).
Struys et al., "Metabolism of Gamma-hydroxybutyrate to d-2-hydroxyglutarate in Mammals: Further Evidence for d-2-hydroxyglutarate Transhydrogenase," Metabolism Clinical and Experimental, 55(3): 353-358 (2006).
Timmins, "Deuterated Drugs; Where are We Now?," Expert Opin Ther Pat, 24(10): 1067-1075 (Oct. 2014).
Verstraete et al., (Problems of Forensic Sciences 2000; XLII: 186-192).
International Preliminary Report on Patentability for International Application No. PCT/US2013/065916 dated May 19, 2015.
International Search Report and Written Opinion for International Application No. PCT/US2013/065916 dated May 22, 2014.
Database PubChem NCBI, Database Accession No. CID4737262 dated Sep. 17, 2005.

(56) References Cited

OTHER PUBLICATIONS

"Understanding Biobased Carbon Content Society of the Plastics Industry Bioplastic Council," Feb. 28, 2012, retrieved from: http://www.plasticsindustry.org/files/about/BPC/Understanding Biobased Content-0212 Date-FINAL.pdf.

Yoshie et al., "Biosynthesis and n.m.r. Studies of Deuterated Poly(3-hydroxybutyrate) Produced by Alcalligenes Eutrophus H16," International Journal of Biological Macromolecules, 14(2): 81-86 (1992).

Zhou et al., "Hyperproduction of poly(4-hydroxybutyrate) from glucose by recombinant *Escherichia coli*", Microbial Cell Factories, Biomed Central, GB, vol. 11, No. 1, p. 54, May 2, 2012.

Office Action from co-pending European Patent Application No. 13802137.3 dated Nov. 25, 2016.

\* cited by examiner

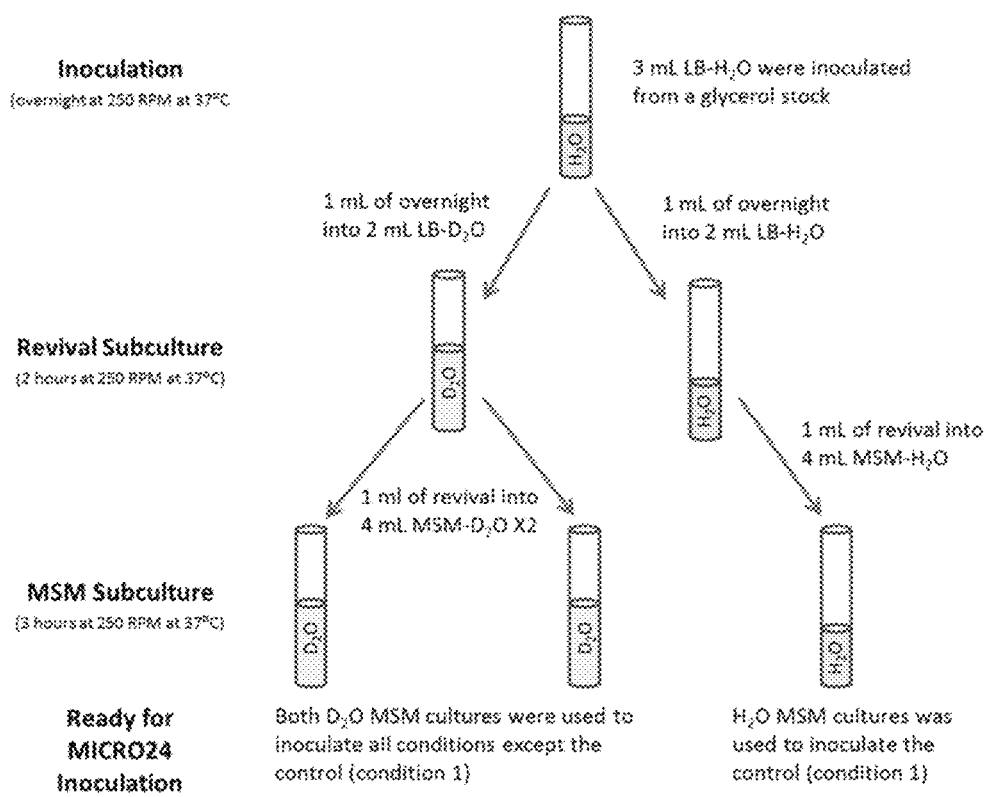

PRODUCTION OF SALTS OF 4-HYDROXYBUTYRATE USING BIOBASED RAW MATERIALS

RELATED APPLICATION(S)

This application is a divisional of U.S. application Ser. No. 14/442,413, filed May 13, 2015, which is the U.S. National Stage of International Application No. PCT/US2013/065916, filed on Oct. 21, 2013, published in English, which claims the benefit of U.S. Provisional Application No. 61/726,294, filed on Nov. 14, 2012, 61/772,602, filed on Mar. 5, 2013, 61/823,518, filed on May 15, 2013 and 61/834,974, filed on Jun. 14, 2013. The entire teachings of the above application(s) are incorporated herein by reference.

FIELD OF THE INVENTION

This invention is in the field of gamma-hydroxybutyrate having a carbon footprint which can be used to identify the source of the gamma-hydroxybutyrate, pharmaceutical compositions containing the traceable gamma-hydroxybutyrate, and methods of use thereof.

BACKGROUND OF THE INVENTION

γ-Hydroxybutyric acid (GHB), also known as 4-hydroxybutanoic acid and sodium oxybate (INN), is a naturally occurring substance found in the human central nervous system, as well as in wine, beef, small citrus fruits, and almost all animals in small amounts. GHB is naturally produced in the human body's cells and is structurally related to the ketone body beta-hydroxybutyrate.

HB has been used in medical settings as a general anesthetic, to treat conditions such as insomnia, clinical depression, narcolepsy, and alcoholism. GHB as the sodium salt, known as sodium oxybate, is sold by Jazz Pharmaceuticals under the name Xyrem to treat cataplexy and excessive daytime sleepiness in patients with narcolepsy.

However, GHB is most well known for it abuse potential. GHB is used illegally as an intoxicant or as a date rape drug. Its effects have been described anecdotally as comparable with alcohol and ecstasy use, such as euphoria, disinhibition, enhanced sensuality and empathogenesis. At higher doses, GHB may induce nausea, dizziness, drowsiness, agitation, visual disturbances, depressed breathing, amnesia, unconsciousness, and death. The effects of GHB can last from 1.5 to 3 hours, or even longer if large doses have been consumed. Consuming GHB with alcohol is dangerous as it can lead to vomiting in combination with unrouseable sleep, a potentially lethal combination. When used as a recreational drug, GHB may be found as the sodium or potassium salt, which is a white crystalline powder, or as GHB salt dissolved in water to form a clear solution. The sodium salt of GHB has a salty taste. Other salt forms such as calcium GHB and magnesium GHB have also been reported, but the sodium salt is by far the most common.

Like alcohol and potent benzodiazepines such as Rohypnol (the trade name of a potent hypnotic benzodiazepine, flunitrazepam), GHB has been labeled as a date rape drug. The sodium form of GHB has an extremely salty taste but, as it is colourless and odorless, it has been described as "very easy to add to drinks" that mask the flavor. GHB has allegedly been used in cases of drug-related sexual assault, usually when the victim is vulnerable due to intoxication with a sedative, generally alcohol. It is difficult to establish how often GHB is used to facilitate rape as it is difficult to detect in a urine sample after a day, and many victims may not recall the rape until some time after this, although GHB can be detected in hair.

There have been several high profile cases of GHB as a date rape drug that received national attention in the United States. In early 1999 a 15 year old girl, Samantha Reid of Rockwood, Mich., died from GHB poisoning. Reid's death inspired the legislation titled the "Hillory J. Farias and Samantha Reid Date-Rape Drug Prohibition Act of 2000." This is the law that made GHB a schedule 1 controlled substance.

GHB has also been used illegally to boost or enhance athletic performance. GHB has been shown to elevate human growth hormone in vivo. The growth hormone elevating effects of GHB are mediated through muscarinic acetylcholine receptors and can be prevented by prior administration of pirenzepine, a muscarinic acetylcholine receptor blocking agent.

GHB can be easily manufactured at home with very little knowledge of chemistry, as it only involves the mixing of its two precursors, GBL and an alkali hydroxide (such as sodium hydroxide) to form the resulting GHB salt. Due to the ease of manufacture and the availability of its precursors, its production is not done in relatively few illicit laboratories like most other synthetic drugs, but in private homes by low level producers instead.

In view of the high abuse potential and ease of manufacture described above, GHB is categorized as an illegal drug in many countries. It is currently regulated in Australia and New Zealand, Canada, most of Europe and in the United States. Therefore, there exists a need to trace the origin or source of GHB so that local, state, and/or federal law enforcement agencies and/or health departments can determine whether the GHB that is used illegally is being produced by a legitimate, approved source or an illegal manufacturer. The ability to produce GHB having a unique fingerprint may allow law enforcement to readily determine the source of a particular sample of GHB.

Therefore, it is an object of the invention to provide traceable gamma-hydroxybutyrate, compositions containing the same, and methods of making and using thereof.

SUMMARY OF THE INVENTION

Gamma-butyrolactone ("GBL") and Gamma-hydroxybutyrate ("GHB") having a unique carbon footprint as defined by the percent modern carbon (pmc) are described herein. The percent modern carbon can be controlled by varying the amounts of biobased, renewable starting materials and petroleum-based starting materials to prepare GBL or GHB having a defined pmc or by preparing mixtures of GBL or GHB prepared from biobased renewable starting materials and GBL or GHB prepared from petroleum-based starting materials.

In one embodiment, gamma-hydroxybutyrate has a pmc of at least about 1% to at least about 99%, for example about 5, 10, 15, 20, 25, 30, 35, 40, 45, 50, 55, 60, 65, 70, 75, 80, 85, 90, or 95%. In particular embodiments, gamma-hydroxybutyrate has a pmc of at least about 80, 81, 82, 83, 84, 85, 86, 87, 88, 89, 90, 91, 92, 93, 94, 95, 95, 97, 98, or 99. In particular embodiments, gamma-hydroxybutyrate has a pmc of at least about 99%. In other embodiments, gamma-hydroxybutyrate can be in the form of a mixture of gamma-hydroxybutyrate prepared from biobased, renewable raw materials and gamma-hydroxybutyrate prepared from petroleum-based materials, wherein the ratio of the two is controlled to provide a unique carbon footprint. The pmc of the mixture can be as described above.

Gamma-hydroxybutyrate can be formulated as the free carboxylic acid, one or more pharmaceutically acceptable base-addition salts, oligomers of gamma-hydroxybutyrate, and pharmaceutically salts of the oligomers. Gamma-hydroxybutyrate and its oligomers, polymers or their salts (e.g. sodium oxybate) can also be modified by substitution of all or some of their hydrogen atoms with deuterium or fluorine atoms. Deuterated gamma-hydroxybutyrate is referred to as DGHB and deuterated gamma-butyrolactone is referred to DGBL. Drug molecules modified in this way reportedly improve either the metabolism of a drug (as is the case with deuterium isotopologues) or the binding affinity of the drug to target receptors (as is the case with fluorine-modified drugs).

Gamma-butyrolactone or deuterated gamma-butryolactone can be converted to gamma-hydroxybutyrate or deuterated gamma-hydrobutyrate by saponification (e.g., base-catalyzed ring opening) of the lactone ring including continuous methods for effecting the ring opening of gamma-butyrolactone or deuterated gammo-butyrolactone to form gamma-hydroxybutyrate or deuterated gamma-hydrobutyrate. Other procedures for producing gamma-hydroxybutyrate or deuterated gamma-hydroxybutyrate include the partial hydrogenation of succinic acid or deuterated forms thereof having a unique carbon footprint and partial oxidation of butanediol or deuterated forms thereof have a unique carbon footprint.

In one embodiment, biobased gamma-butyrolactone or deuterated gamma-butyrolactone having a unique carbon footprint is produced from the conversion to biobased GHB or DGHB having a unique carbon footprint by pyrolysis of poly(4-hydroxybutyrate) or deuterated poly(4-hydroxybutyrate).

P4HB or deuterated forms thereof ("DP4HB") can be produced from a variety of biobased, renewable raw materials, such as glucose or deuterated glucose syrup using fermentation methods. P4HB or DP4HB can also be prepared from a mixture of biobased, renewable raw materials and petroleum-based raw materials using the same fermentation procedures. In some embodiments, deuterated glucose and/or deuterated water can be used as the deuterium source.

P4HB or DP4HB can be pyrolyzed in the presence of $Ca(OH)_2$ to produce GBL or DGBL, which can be saponified to form GHB or DGHB. P4HB or DP4HB can also be converted to GHB or DGHB by dissolving purified P4HB or DP4HB in an organic solvent, such as tetrahydrofuran (THF), and reacted with a base, such as sodium methoxide, to convert P4HB or DP4HB directly to GHB or DGHB. The same procedure can also be used to prepare 4HB or D4HB oligomers of a desired molecular weight. Biobased GBL or DGBL or a mixture of biobased GBL or DGBL and petroleum-based GBL or DGBL can be converted to GHB or DGHB by reacting GBL or DGBL with a base, such as sodium hydroxide, to form the sodium salt of gamma-hydroxybutyric acid, sodium gamma-hydroxybutyrate or deuterated gamma-hydrobutyrate.

GBL or GBH or deuterated forms thereof having a unique carbon footprint can be prepared from succinic acid or deuterated forms thereof. Succinic acid having a particular carbon footprint can be prepared by fermentation of microbial biomass, isolation of the succinic acid, and catalytic hydrogenation of succinic acid to form GHB.

GHB having a unique footprint can also be prepared from 1,4-butanediol or deuterated forms thereof having the unique carbon footprint. 1,4-butanediol having a particular carbon footprint can be prepared by fermentation of microbial biomass, isolation of the 1,4-butanediol, and catalytic oxidation of 1,4-butane diol to form GHB.

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

By producing GBL or GHB or deuterated forms thereof having a unique carbon footprint as defined by the pmc, law enforcement agencies can identify the source of GBL or GHB as well as track shipments of the materials from site of manufacture to end user. The footprint can be used to confirm whether a sample was prepared by a legitimate manufacturer or an illegal drug lab.

BRIEF DESCRIPTION OF THE DRAWINGS

FIG. 1 is a flow chart showing the steps for the synthesis of deuterated P4HB using $D_2O$ or deuterated glucose as the deuterium source.

DETAILED DESCRIPTION OF THE INVENTION

I. Definitions

"Biobased content", as used herein, refers to the amount of biomass-derived carbon in a sample of gamma-hydroxybutyrate ("GHB"). The biobased content can be determined using techniques known in the art, such as ASTM-D6888. The biobased content can be determined by deriving the ratio of the amount of $^{14}C$ in an unknown sample to that of a modern reference standard. This ratio is calculated as a percentage with the units "pmc" (percent modern carbon). If the material being analyzed is a mixture of present day radiocarbon and fossil carbon (containing no radio carbon), then the pmc value correlates directly to the amount of biomass derived carbon in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). For an archaeologist or geologist using radiocarbon dates, AD 1950 equals "zero years old". It also represents 100 pMC.

"Bomb carbon" in the atmosphere reached almost twice normal levels in 1963 at the peak of testing and prior to the treaty halting testing. Its distribution within the atmosphere has been approximated since its appearance, showing values that are greater than 100 pMC for plants and animals living since AD 1950. It has gradually decreased over time with today's value being near 105 pMC. This means that a fresh biomass material such as corn, sugar cane or soybeans would give a radiocarbon signature near 105 pMC. Combining fossil carbon with present day carbon into a material will result in a dilution of the present day pMC content. By presuming ~105 pMC represents present day biomass materials and 0 pMC represents petroleum derivatives, the measured pMC value for that material will reflect the proportions of the two component types. For example, a material derived 100% from present day soybeans would give a radiocarbon signature near 105 pMC. But if it was diluted with 50% petroleum carbon, it would give a radiocarbon signature near 53 pMC.

The "biobased content" of a material is reported as a percent value relating total renewable organic carbon to total organic carbon. The final result is calculated by multiplying the pMC value measured for the material by 0.95 (to adjust for bomb carbon effect). The final value is cited as the MEAN BIOBASED RESULT and assumes all the components within the analyzed material were either present day living (within the last decade) or fossil in origin.

"Effective amount" as generally used herein refers to an amount, or dose, within the range normally given or prescribed to demonstrate an effect, e.g., in vitro or in vivo. The range of an effective amount may vary from individual to individual; however, the optimal dose is readily determinable by those of skill in the art depending upon the use. Such ranges are well established in routine clinical practice and will thus be readily determinable to those of skill in the art. Doses may be measured by total amount given (e.g. per dose or per day) or by concentration. Doses of 0.01, 0.05, 0.1, 0.5, 1, 2, 3, 4, 5, 6, 7, 8, 9, 10, 15, 20, 25, 30, 40, 50, 100, 500 and 1000 mg/kg/day may be appropriate for treatment.

"Pharmaceutically acceptable" as generally used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

II. Gamma-Hydroxybutyrate

Gamma-hydroxybutyrate has the following chemical structure:

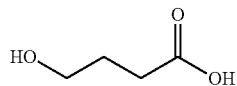

Gamma-hydroxybutyrate or deuterated forms thereof produced from biobased raw materials, alone or in combination with fossil-fuel derived or petroleum-based raw materials are described herein. By varying the amounts of biobased raw material and fossil-fuel derived material, one can produce gamma-hydroxybutyrate have a unique carbon footprint or signature which can be used as a means for identifying the source of the gamma-hydroxybutyrate (i.e., the manufacturer) as well as tracking its shipping and usage. This footprint is derived from the ratio of modern carbon, which is incorporated from the biobased raw materials to fossil carbon, which is derived from petroleum-based raw materials and is express as the percent modern carbon or pmc.

In one embodiment, gamma-hydroxybutyrate has a pmc of at least about 1% to at least about 99%, for example about 5, 10, 15, 20, 25, 30, 35, 40, 45, 50, 55, 60, 65, 70, 75, 80, 85, 90, or 95%. In particular embodiments, gamma-hydroxybutyrate has a pmc of at least about 80, 81, 82, 83, 84, 85, 86, 87, 88, 89, 90, 91, 92, 93, 94, 95, 95, 97, 98, or 99. In particular embodiments, gamma-hydroxybutyrate has a pmc of at least about 99%. In other embodiments, gamma-hydroxybutyrate can be in the form of a mixture of gamma-hydroxybutyrate prepared from biobased, renewable raw materials and gamma-hydroxybutyrate prepared from petroleum-based materials, wherein the ratio of the two is controlled to provide a unique carbon footprint. The pmc of the mixture can be as described above.

Gamma-hydroxybutyrate can be formulated as the free carboxylic acid, one or more pharmaceutically acceptable base-addition salts, oligomers of gamma-hydroxybutyrate, and pharmaceutically salts of the oligomers.

"Pharmaceutically acceptable salts" as generally used herein refer to derivatives of the disclosed compounds wherein the parent compound is modified by making the base salt thereof. Examples of pharmaceutically acceptable salts include, but are not limited to, alkali or organic salts of acidic residues such as carboxylic acids. Suitable salts include, but are not limited to, Group I metals, such as sodium and potassium, and Group II metals, such as magnesium and calcium.

The gamma-hydroxybutyrate can also be formulated an oligomer or polymer of gamma-hydroxybutyrate. "Oligomer", as used herein, generally refers to polymers having 2-10 repeat units, while "polymer" as used herein, generally refers to polymers having at more than 10 repeat units. The preferred compositions may contain GHB alone, as in a homopolymer (or oligomer) of gamma-hydroxybutyrate, or may comprise GHB in a polymer or oligomer together with other monomers. For example, GHB may be copolymerized with β-hydroxybutyrate, as in poly-β-hydroxybutyrate-co-γ-hydroxybutyrate, or copolymerized with two or more different monomers, including other hydroxyalkanoates or hydroxyacids. Examples of monomers which can be incorporated into GHB polymers and oligomers are identified in Williams, et. al., *Int. J. Biol. Macromol.*, 25:111-21 (1999).

In addition to linear oligomers comprising GHB, cyclic oligomers comprising GHB may be especially useful for delivery of GHB in vivo. These may be prepared, for example, according to procedures described in Müller & Seebach, *Angew. Chem. Int. Ed. Engl.* 32:477-502 (1993).

In a further embodiment, polymers and oligomers may be prepared that do not contain GHB, but break down in vivo to GHB. An example of such a polymer is the bioerodible polyorthoester described in Sendelbeck & Girdis, *Drug Metabolism & Disposition*, 13:291-95 (1985).

The oligomers and polymers can be formulated as a salt of the oligomer or polymer or can be virtually or completely salt free. The oligomers and/or polymers can deliver GHB with a range of different and desirable pharmacokinetics. This includes prolonged release, steady state release, and controlled dosages, both low and high.

Gamma-hydroxybutyrate and/or oligomers and/or polymers thereof and/or deuterated forms thereof can be formulated for controlled release, such as immediate release, extended release, delayed release, pulsatile release, or combinations thereof. In some embodiments, the molecular weight range of the oligomer or polymer is from about 500 Daltons to about 50,000 Dalton, preferably from about 500 Dalton to about 25,000 Daltons, more preferably from about 500 Daltons to about 15,000 Dalton, most preferably from about 500 Daltons to about 10,000 Daltons. In some embodiments, the composition can contain two or more oligomers of polymers having different weight average molecular weights. For example, in one embodiment, the composition contains a first oligomer/polymer having a weight average molecular weight of from about 500 to about 2,000 Daltons and a second oligomer/polymer having a weight average molecular weight from about 2,000 to about 10,000 Daltons.

In other embodiments, the composition can contain oligomers saturated with a salt of 4HB or GBL such that the dosing of 4HB is biphasic with a first rapid release followed by a slow release from the oligomers to achieve a single does when administered at night (e.g., before bed).

The use of oligomers and polymer can overcome some limitations sometimes associated with use of the monomer. For example, the development of hypernatremia and metabolic alkalosis has been reported as a result of delivering large doses of GHB when administered as the sodium salt rather than a free acid, especially over prolonged periods. It has been reported that these conditions developed in patients undergoing hemodialysis. The use of oligomers or polymers of GHB can reduce the amount of sodium ion administered and therefore avoid the side effects associated with high concentrations of sodium ion.

In addition to problems associated with the delivery of the sodium salt form of GHB, the half-life of GHB is relatively short (35 minutes, with peak plasma concentration occurring 20-60 minutes after oral administration), requiring more frequent administration of GHB to maintain its therapeutic effects. For example, it has been reported that increasing the dosing of GHB from three times a day to six times a day was beneficial in the treatment of alcoholism, particularly for a patient population which did not respond well to less frequent dosages. Furthermore, in the treatment of narcoleptic patients, patients were found to benefit from two, or even three, doses of GHB during the night instead of a single dose which left patients wide awake before their planned awakening time (Scharf, *Sleep*, 21:507-14 (1998)). Also, oligomers/polymers are not readily dissolved in drinks such as soda, fruit juices or alcoholic beverages which should reduce abuse potential.

In another embodiment, GHB and its oligomers, polymers and salt forms can be modified by substituting some or all of its hydrogen atoms with deuterium or fluorine. Complete or partial substitution of the hydrogen atoms with deuterium in drug molecules has been shown to positively affect the medicinal properties of drugs. In particular, the metabolism rates of drug molecules have been shown to change since C—H bonds are weaker than C-D (the deuterium atom is twice as heavy), metabolic reactions that rely on breaking such bonds in their rate-limiting step are slowed, even though in other chemical and pharmacological aspects there are no significant differences observed. Several companies are pursuing this area of research and include Concert Pharmaceuticals, Protia and Auspex.

Methods for creating deuterated analogs of organic compounds are described in the following patents: U.S. Pat. No. 5,221,768 describes how to deuterate hydroxyacids using heavy water ($D_2O$) with a rhodium chloride (III) catalyst. The mixture is then moderately heated under pressure to initiate the hydrogen-deuterium exchange. U.S. Pat. No. 4,421,865 describes the use of ion exchange columns to deuterate organic molecules. Patent Appl. No. US2012/122,952 describes how to produce a deuterated analog of GHB by first starting with the t-butyl ester of 4-hydroxybutyrate (prepared from succunic acid) and then reacting it in deuterated methanol in the presence of potassium carbonate. After hydrogen-deuterium exchange is complete, the compound is saponified with sodium hydroxide to form deuterated sodium oxybate. A final method to produce biobased, deuterated GHB is to feed deuterated glucose (d-glucose) to engineered microbes which produce P4HB polymer or to carry out the fermentation in $D_2O$ with or without D-glucose as the feed. The polymer so produced would have deuterium replacing most if not all of the hydrogen atoms. Deuterated-GBL (d-GBL) could then be prepared from the polymer as described previously (through pyrolysis) and the d-GBL converted to d-sodium oxybate by saponification. Methods for creating fluorinated analogs of organic compounds are described in International Patent No. WO2012/214162.

A. Other Compounds Derived from GBL or Deuterated GBL

Other compounds having a unique carbon footprint can be prepared from GBL or deuterated GBL. Compounds having a unique footprint which can be prepared from GBL or deuterated GBL include, but are not limited to, poly(4-hydroxybutyrate) or deuterated poly(4-hydroxybutyrate), 2-pyrrolidone or deuterated 2-pyrrolidone, 1,4-butanediol or deuterated 1,4-butanediol, tetrahydrofuran (THF) or deuterated THF, n-methylpyrrolidone (NMP) or deuterated NMP, n-ethylpyrrolidone (NEP) or deuterated NEP, n-vinylpyrrolidone (NVP) or deuterated (NVP) and polyvinylpyrrolidone (PVP) or deuterated PVP. These compounds can be used as active agents, excipients, and/or solvents in pharmaceutical formulations as described below. In other embodiments, one or more of these compounds are precursors for one or more active agents. For example, 2-pyrrolidone is a precursor to the active agents Cotinine, Doxapram, Piracetam, Povidone, and Ethosuximide.

B. Derivatives of 4-Hydroxybutyrate (4HB)

Derivatives of 4HB having a unique carbon footprint can also be prepared. Exemplary derivatives are described, for example, in U.S. Pat. No. 8,461,197 to Tung, which is incorporated herein by reference and includes compounds represented by Formulae B, B-II, B-III, I, II, S-II, and III. Compounds having a unique carbon footprint may contain no deuterium, one deuterium or more than one deuterium.

Deuterated P4HB polymers can also be produced using the methods described herein and are useful in a range of biomedical applications including fibers used for sutures and meshes as described in U.S. Pat. Nos. 6,245,537; 6,610,764; 6,548,569; 6,623,730; 8,034,270; as well as other patents assigned to Tepha, Inc, all of which are incorporated herein by reference.

III. Formulations

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Xyrem®, marketed by Jazz Pharmaceuticals, is a solution of GHB for oral administration. The pH of the solution is carefully controlled to resist microbial growth and prevent degradation of GHB into GBL or other substances.

The pH may be from about 3.0 to about 10.3, or about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, or about 10.3, and all pH values between each of the listed pH values, of the aqueous media. In some embodiments, the pH is between about 6 and 8.5, for example, 7.5 to 8.5. This will produce a GHB composition that is resistant to microbial growth as defined by the test described herein.

These pH values will produce compositions resistant to microbial growth in an aqueous medium if the amount of GHB added, admixed, or dissolved is from above about 150 mg/ml to about 450 mg/ml, namely, above about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml, about 260 mg/ml, about 270 mg/ml, about 280 mg/ml, about 290 mg/ml, about 300 mg/ml, about 310 mg/ml, about 320 mg/ml, about 330 mg/ml, about 340 mg/ml, about 350 mg/ml, about 360 mg/ml, about 370 mg/ml, about 380 mg/ml, about 390 mg/ml, about 400 mg/ml, about 410 mg/ml, about 420 mg/ml, about 430 mg/ml, about 440 mg/ml, to about 450 mg/ml, and all amounts of GHB between the values listed.

The composition may also contain a pH adjusting or buffering agent. Such agents may be acids, bases, or combinations thereof. In certain embodiments, the acid may be an organic acid, preferably a carboxylic acid or alphahydroxy carboxylic acid. In certain other embodiments, the acid is selected from the group including, but not limited to, acetic, acetylsalicylic, barbital, barbituric, benzoic, benzyl penicillin, boric, caffeine, carbonic, citric, dichloroacetic, ethylenediaminetetra-acetic acid (EDTA), formic, glycerophosphoric, glycine, lactic, malic, mandelic, monochloroacetic, oxalic, phenobarbital, phenol, picric, propionic, saccharin, salicylic, sodium dihydrogen phosphate, succinic, sulfadiazine, sulfamerazine, sulfapyridine, sulfathiazole, tartaric, trichloroacetic, and the like, or inorganic acids such as hydrochloric, nitric, phosphoric or sulfuric, and the like. In a preferred embodiment, the acid is malic or hydrochloric acid. In certain other embodiments, the pH adjusting agent may be a base selected from the group including, but not limited to, acetanilide, ammonia, apomorphine, atropine, benzocaine, caffeine, calcium hydroxide, cocaine, codeine, ephedrine, morphine, papaverine, physostigmine, pilocarpine, potassium bicarbonate, potassium hydroxide, procaine, quinine, reserpine, sodium bicarbonate, sodium dihydrogen phosphate, sodium citrate, sodium taitrate, sodium carbonate, sodium hydroxide, theobromine, thiourea or urea. In certain other embodiments, the pH adjusting agent may be a mixture of more than one acid and/or more than one base. In other preferred embodiments, a weak acid and its conjugate base are used to form a buffering agent to help stabilize the composition's pH.

In certain embodiments, the composition may contain one or more salts. A "salt" is understood herein to mean certain embodiments to mean a compound formed by the interaction of an acid and a base, the hydrogen atoms of the acid being replaced by the positive ion of the base. Various salts, including salts of GHB, are contemplated, particularly as pH adjusting or buffering agents. Pharmaceutically acceptable salts, include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropyamine, trimethylamine, histidine, procaine and the like. Alkali metal salts such as lithium, potassium, sodium, and the like may be used, preferably with an acid to form a pH adjusting agent. Other salts include ammonium, calcium, magnesium and the like. In one embodiment, a salt of GHB containing an alkali metal may be combined with an acid to create a composition that achieves the desired pH when admixed with an aqueous medium. In another embodiment, a weak base may be combined with GHB to create a composition that achieves the desired pH when admixed with an aqueous solution. Of course, other salts can be formed from compounds disclosed herein, or as would be known to one of ordinary skill in the art, and all such salts are contemplated.

In certain embodiments, excipients may be added to the composition. An "excipient" as used herein shall mean certain embodiments which are more or less inert substances added as diluents or vehicles or to give form or consistency when the remedy is in a solid form, though they may be contained in liquid form preparations, e.g. syrups, aromatic powders, honey, and various elixirs. Excipients may also enhance resistance to microbial growth, and thus act as a preservative. Such excipients include, but are not limited to, xylitol, mannitol, lactose, starch, magnesium stearate, sodium saccharine, cellulose, cellulose derivatives, magnesium carbonate and the like.

In certain embodiments, the pharmaceutical composition may contain a preservative. A "preservative" is understood herein to mean certain embodiments which are substances added to inhibit chemical change or microbial action. Such preservatives may include, but are not limited to, xylitol, sodium benzoate, methylparaben, propyl gallate BP, sorbic acid, chlorobutanol, dihydroacetic acid, monothioglycerol, potassium benzoate, propylparaben, benzoic acid, benzalkonium chloride, alcohol, benzoic acid, benzalkonium chloride, benzethonium chloride, benzyl alcohol, butylparaben, cetylpyridinium chloride, ethylenediamine, ethylparaben, ethyl vanillin, glycerin, hypophosphorus acid, methylparaben, phenol, phenylethyl alcohol, phenylmercuric nitrate, propylparaben, sassafras oil, sodium benzoate, sodium propionate, thimerosal and potassium sorbate. Preferred preservatives may be selected from the group comprising, but not limited to, xylitol, sodium benzoate, methylparaben, propylparaben and potassium sorbate. Xylitol is particularly preferred in certain compositions of the invention, because it acts as a preservative and a sweetener, is a caries preventative, is less laxative than other sweeteners, and is recommended for diabetics.

In certain embodiments, the pharmaceutical composition may also contain an antioxidant. An "antioxidant" is understood herein to mean certain embodiments which are substances that inhibit oxidation. Such antioxidants include, but are not limited to, ascorbyl palmitate, butylated hydroxyanisole, butylated hydroxytoluene, potassium metabisulfite, sodium metabisulfite, anoxomer and maleic acid BP.

In certain embodiments, the pharmaceutical composition may also contain a flavoring agent. A "flavoring agent" is understood herein to mean certain embodiments which are substances that alters the flavor of the composition during oral consumption. A type of "flavoring agent" would be a sweetener. Preferred sweeteners or flavoring agents would be microbially non-metabolizable. Especially preferred sweeteners or flavoring agents would be carbohydrates such as xylitol and sorbitol. Such flavoring agents include, but are not limited to, acacia syrup, anethole, anise oil, aromatic elixir, benzaldehyde, benzaldehyde elixir-compound, caraway, caraway oil, cardamom oil, cardamom seed, cardamom spirit, cardamom tincture-compound, cherry juice, cherry syrup, cinnamon, cinnamon oil, cinnamon water, citric acid, citric acid syrup, clove oil, coca, coca syrup. coriander oil, dextrose, eriodictyon, eriodictyon fluidextract, eriodictyon syrup aromatic, ethyl acetate, ethyl, vanillin, fennel oil, ginger, ginger fluidextract, ginger oleoresin, glucose, glycerin, glycyrrhiza, glycyrrhiza elixir, glycyrrhiza extract, glycyrrhiza extract-pure, glycyrrhiza fluidextract, glycyrrhiza syrup, honey, non-alcoholic elixir, lavender oil, citrus extract or oil, lemon oil, lemon tincture, mannitol, methyl salicylate, nutmeg oil, orange-bitter-elixir, orange-bitter-oil, orange flower oil, orange flower water, orange oil, orange peel-bitter, orange-peel-sweet-tincture, orange spirit-compound, compound, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sorbitol solution, spearmint, spearmint oil, sucrose, syrup, thyme oil, tolu balsam, tolu balsam syrup, vanilla, vanilla tincture, vanillin or wild cherry syrup.

Specific formulations are described in U.S. Pat. Nos. 6,780,889; 7,262,219; 7,851,506; and U.S. Pat. No. 8,263,650 to Cook et al., the contents of which are incorporated herein by reference.

1. Controlled Release Formulations

The parenteral formulations described herein can be formulated for controlled release including immediate release, delayed release, extended release, pulsatile release, and combinations thereof.

i. Nano- and Microparticles

For parenteral administration, the gamma-hydroxybutyrate, and optional one or more additional active agents, can be incorporated into microparticles, nanoparticles, or combinations thereof that provide controlled release of the gamma-hydroxybutyrate and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the gamma-hydroxybutyrate and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof. Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten. Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of the gamma-hydroxybutyrate to a patient in need thereof. For intravenous or intraarterial routes, this can be accomplished using drip systems, such as by intravenous administration. For topical applications, repeated application can be done or a patch can be used to provide continuous administration of the gamma-hydroxybutyrate over an extended period of time.

2. Injectable/Implantable Solid Implants

The gamma-hydroxybutyrate described herein can be incorporated into injectable/implantable solid or semi-solid implants, such as polymeric implants. In one embodiment, the gamma-hydroxybutyrate are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the gamma-hydroxybutyrate can be incorporated into a polymer matrix and molded, compressed, or extruded into a device that is a solid at room temperature. For example, the gamma-hydroxybutyrate can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more gamma-hydroxybutyrate from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the gamma-hydroxybutyrate from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

In some embodiments, the formulation is in the form of a solid dosage form, such as a capsule or tablet, wherein the formulation is an immediate release dosage form releasing at least 85, 86, 87, 88, 89, 90, 91, 92, 93, 94, or 95% of the gamma hydroxybutyrate in less than an hour as measured in de-ionized water using USP Apparatus 2 at 37° C.±2° C. with paddles at 50 rpm.

1. Controlled Release Formulations

Oral dosage forms, such as capsules, tablets, solutions, and suspensions, can be formulated for controlled release. For example, the gamma-hydroxybutyrate and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the gamma-hydroxybutyrate and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the gamma-hydroxybutyrate, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the gamma-hydroxybutyrate and/or additional active agents.

i. Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids. The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

In some embodiments, the formulation is a controlled release formulation in the form of a solid dosage form, such as a capsule or tablet. The formulation can contain a core containing gamma hydroxybutyrate or a salt thereof and one or more materials, such as polymeric materials, which provide controlled release of the gamma hydroxybutyrate. The core can release the release the gamma hydroxybutyrate over an extended period of time, e.g., greater than 2, 3, 4, 6, 7, or 8 hours, preferably 6-8 hours. The formulation can also contain an immediate release coating containing gamma hydroxybutyrate which releases a substantial portion (greater than 85, 86, 87, 88, 89, 90, 91, 92, 93, 94, or 95%) of the gamma hydroxybutyrate in less than an hour as measured in de-ionized water using USP Apparatus 2 at 37° C.±2° C. with paddles at 50 rpm.

ii. Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The P4HB polymer, deuterated P4HB polymer, 4HB oligomers or deuterated 4HB oligomers may be used as the coating material with the added benefit that they are also a source of the 4-HB. For example, a coating containing one or more of the above can be applied to a solid dosage form such as a tablet or capsule to provide immediate release and/or controlled release of 4HB.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof "Emollients" are an externally applied agent that softens or soothes skin and are generally known in the art and listed in compendia, such as the "Handbook of Pharmaceutical Excipients", 4th Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of gamma-hydroxybutyrate to a patient in need thereof. For topical applications, repeated application can be done or a patch can be used to provide continuous administration of the gamma-hydroxybutyrate over an extended period of time.

D. Pulmonary Formulations

In one embodiment, the gamma-hydroxybutyrate are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids.

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. The deep lung, or alveoli, are the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration olf therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm3, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solutions is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the gamma-hydroxybutyrate hydroxybutyrate or oligomers of gamma-hydroxybutyrate. An appropriate solvent should be used that dissolves the gamma-hydroxybutyrate hydroxybutyrate or oligomers of gamma-hydroxybutyrate or forms a suspension of the gamma-hydroxybutyrate. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the gamma-hydroxybutyrate in the lungs and that the excipients that are present are present in amount that do not adversely affect uptake of gamma-hydroxybutyrate in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

IV. Methods of Making Gamma-Hydroxybutyrate

Gamma-hydroxybutyrate or deuterated gamma-hydrobutyrate having a unique carbon footprint can be prepared by a variety of techniques. In one embodiment, gamma-butyrolactone or deuterated gamma-hydrobutyrate is prepared having a particular percentage of modern carbon. This can be done through a variety of procedures, including fermentation. By using biobased renewable raw materials and petroleum-based raw materials in defined ratios, one can prepare gamma-butyrolactone or deuterated gamma-hydrobutyrate having a unique carbon footprint and therefore can be traced. Gamma-butyrolactone or deuterated gamma-butyrolactone can be converted to gamma-hydroxybutyrate or deuterated gamma-hydroxybutyrate by saponification (e.g., base-catalyzed ring opening) of the lactone ring. U.S. Patent Application Publication No. 2011/0028551, the contents of which are incorporated herein, describes continuous methods for effecting the ring opening of gamma-butyrolactone to form gamma-hydroxybutyrate. Other procedures for producing gamma-hydroxybutyrate or deuterated gamma-hydrobutyrate include the partial hydrogenation of succinic acid or deuterated forms thereof having a unique carbon footprint and partial oxidation of butanediol or deuterated forms thereof have a unique carbon footprint.

In one embodiment, biobased gamma-butyrolactone is produced from the conversion to biobased GHB or deuterated gamma-hydrobutyrate by pyrolysis of poly(4-hydroxybutyrate) or DP4HB as described in WO 2011/100601 P4HB or DP4HB can be produced from a variety of biobased, renewable raw materials, such as glucose or deuterated glucose syrup or $D_2O$ using fermentation methods. P4HB or DP4Hb can also be prepared from a mixture of biobased, renewable raw materials and petroleum-based raw materials using the same fermentation procedures. P4HB or DP4HB can be pyrolyzed in the presence of $Ca(OH)_2$ to produce GBL or DGBL, which can be saponified to form GHB or DGHB. P4HB or DP4HB can also be converted to GHB or DGHB by dissolving purified P4HB or DP4HB in an organic solvent, such as tetrahydrofuran (THF), and reacted with a base, such as sodium methoxide, to convert P4HB or DP4Hb directly to GHB or DGHB. The same procedure can also be used to prepare 4HB or D4HB oligomers of a desired molecular weight. Biobased GBL or DGBL or a mixture of biobased GBL or DGBL and petroleum-based GBL or DGBL can be converted to GHB or DGHB by reacting GBL or DGBL with a base, such as sodium hydroxide, to form the sodium salt of gamma-hydroxybutyric acid or deuterated gamma-hydrobutyrate, sodium gamma-hydroxybutyrate or deuterated sodium gamma-hydrobutyrate.

GBL or GBH or deuterated forms thereof having a unique carbon footprint can be prepared from succinic acid or deuterated forms thereof. Succinic acid having a particular carbon footprint can be prepared by fermentation of microbial biomass, isolation of the succinic acid, and catalytic hydrogenation of succinic acid to form GHB.

GHB or DGHB having a unique footprint can also be prepared from 1,4-butanediol or deuterated forms thereof having the unique carbon footprint. 1,4-butanediol having a particular carbon footprint can be prepared by fermentation of microbial biomass, isolation of the 1,4-butanediol, and catalytic oxidation of 1,4-butane diol to form GHB.

GBL or GHB or deuterated forms thereof can be produced in very high purity, for example, greater than 95%, 96%, 97%, 98%, 99%, 99.1%, 99.2%, 99.3%, 99.4%, 99.5%, 99.5%, 99.6%, 99.7%, 99.8%, or 99.9% on a mass basis which requires less purification to prepare a product for pharmaceutical compositions.

Methods for making a variety of deuterated compounds via growth of bacteria in deuterated media is described in WO 1997/007216, which is incorporated herein by reference. Compounds having a unique carbon footprint can be prepared using the techniques described therein.

V. Methods of Use of Gamma-Hydroxybutyrate

Gamma-hydroxybutyrate ("GHB") is a naturally occurring substance that is widely distributed in the mammalian body, being present, for example, in the brain, kidney, heart, liver, lung and muscle. When administered exogenously, GHB readily crosses the blood-brain barrier and penetrates the brain, producing a number of neuropharmacological effects. GHB has been used as an intravenous agent for the induction of anesthesia and for long-term sedation, without serious side-effects on circulation or respiration, and without an accompanying seizure-inducing activity in humans. It has also been suggested that GHB may be a suitable agent for total intravenous anesthesia in patients with coronary artery disease, as well as for sedation during spinal anesthesia. Patients with chronic schizophrenia characterized by autism, inactivity, and apathy; catatonic schizophrenia; chronic schizophrenia with hallucination and delusion; atypical psychoses; and chronic brain syndrome due to trauma, as well as neurotic patients have all been treated using GHB.

In addition to these uses, GHB also is used to treat narcolepsy, a chronic sleep disorder that usually begins in adolescence or early adulthood and lasts throughout life. Narcolepsy is characterized by sudden sleep attacks lasting usually from a few to thirty minutes, paralysis upon lying down or waking, visual or auditory hallucinations at the onset of sleep, and temporary loss of muscle tone while awake (cataplexy) or asleep. Treatment with GHB substantially reduces these signs and symptoms of narcolepsy in humans. GHB as the sodium salt, known as sodium oxybate, is sold by Jazz Pharmaceuticals under the name Xyrem to treat cataplexy and excessive daytime sleepiness in patients with narcolepsy.

Other uses of GHB include its application in the pharmacotherapy of alcoholism, where it has been found to reduce alcohol craving and consumption, and to ameliorate symptoms of alcohol withdrawal syndrome in alcoholics. GHB also reportedly aids patients undergoing withdrawal from opiates and relieves anxiety, tremor, and muscle rigidity in patients with Parkinson's disease.

Administration of GHB also has been reported to protect neurons and intestinal epithelium against cell death resulting from experimental ischemia, to drop blood pressure in hypertensive patients, to increase plasma levels of growth hormone after injection in healthy subjects, and to stimulate growth hormone and prolactin production. Administration of GHB also is purported to be an effective anorectic, heighten sexual desire, produce pleasurable effects such as euphoria and smooth muscle relaxation, promote muscle mass, and be able to induce rapid eye movement sleep. PCT WO 99/09972 and U.S. Pat. No. 5,990,162 to Scharf discloses the use of GHB in the treatment of fibromyalgia and chronic fatigue syndrome. Administration of GHB also has been shown to increase gastric emptying, and could be used as a prokinetic drug for treatment of a number of conditions where improvement in gastrointestinal motility and gastric emptying is desired. Such conditions include treatment of malabsorption disorders, and increased uptake of poorly absorbed drugs. Gamma-butyrolactone which is metabolized to GHB has been shown to potentiate the effect of gamma-aminobutyric acid on gastric secretions. GHB has shown anti-ulcer activity against ulcers induced by indomethacin, restraint stress or pyloric ligation.

In animals, GHB produces electroencephalographic (EEG) and behavioral changes, resembling generalized absence seizures. The treated animals show arrest of activity which can be aborted by anti-absence drugs. For this reason, GHB has been used to provide a reproducible, consistent, pharmacologically specific model for the study of generalized absence seizures, which is analogous to other models of absence in the rat. GHB administration also has been used in animals to normalize cardiovascular function of hemorrhage and as an anti-ischemic. In mice, GHB was found to exert a radioprotective effect.

Infusion of GHB also has been found to possess an angiogenesis inhibitory effect, making GHB potentially useful in the treatment of cancer as an anti-angiogenesis agent. GHB also has been used prophylactically in rats as an antihypoxant, antioxidant, or actoprotector, increasing survival rates of rats with myocardial infarction. GHB reportedly prevents heart damage after acute blood loss.

GHB may also be administered prophylactically to reduce inflammation or ischemic or reperfusion injury during surgery. Prophylactic administration of GHB prevented liver damage to tetrachloromethane poisoning. The lithium salt of GHB depressed carrageenan inflammation in a hamster cheek pouch assay. Prophylactic administration of lithium salt of GHB prevented inflammation in acute paw edema assay. GHB has been shown to improve blood flow to ischemic heart tissue. GHB also has been used to protect frozen liver tissue for transplantation.

Sodium 4-hydroxybutyrate has been shown to affect metabolism, as its administration reduced nucleotide catabolism, glycolysis, lipolysis, and lipid peroxidation. Sodium hydroxybutyrate also has been shown to stimulate the pentosophosphate cycle and interfere with metabolic acidosis. Thus GHB may be used to improve metabolism and to offset the damaging effects of injury, surgery, ischemia and shock.

GHB has been shown to prevent the proliferation of cancer and functions as an antineoplastic agent (Basaki, et al., *Gan To Kagaku Ryoho*, 27:93-98 2000)). GHB and gamma-butyrolactone have been shown to reduce angiogenesis induced by certain types of cancer cells (Yonekura, et al., *Clinical Cancer Research*, 5:2185-91 (1999)). GHB also has been shown to be beneficial for the treatment of lung cancer patients during and after surgery (Leonenkov, et al., *Vopr. Onkol.*, 39:75-79 (1993)) and this benefit was attributed to the antihypoxic effects of GHB. Accordingly, GHB can be used to prevent the spread or proliferation of a cancer.

The compositions described herein can contain a single active component, a plurality of active components, and/or one or more components which can be converted to an active component. For example, the compositions described herein can contain GHB or DGHB alone or in combination with GBL, DGBL, P4HB, DP4HB, or combinations thereof. In other embodiments, the composition contains GBL or DGBL in combination with P4HB or DP4HB. In still other embodiments, the composition contains oligomers of GBL or DGBL in combination with P4HB or DP4HB and monomeric GBL or DGBL. The compositions can be formulated for controlled release, such as immediate release, extended release, delayed release, pulsatile release, and combinations thereof. For example, the composition can be in the form of a tablet or capsule with a coating containing the active agent for immediate release and a core (tablet) or fill (capsule) which provides extended release or delayed release.

EXAMPLES

Example 1. Production of Biobased Gamma-Butyrolactone (GBL) from the Pyrolysis of a Genetically Engineered Microbe Producing Poly-4-Hydroxybutyrate (P4HB)

In this example biobased GBL is produced for the conversion to Biobased GHB for use in pharmaceutical applications with improved monitoring and safety. Biomass containing poly-4-hydroxybutyrate (poly-4HB) was produced in a 20 L New Brunswick Scientific fermentor (BioFlo 4500) using a genetically modified *E. coli* strain specifically designed for high yield production of poly-4HB from glucose syrup as the sole carbon feed source. The use of a renewable resource based feedstock such as glucose syrup as the sole carbon source enables the production of a biobased P4HB and hence the production of biobased GBL and derivatives including biobased gamma-hydroxybutyric acid (GHB). Examples of the *E. coli* strains, fermentation conditions, media and feed conditions are described in U.S. Pat. Nos. 6,316,262; 6,689,589; 7,081,357; and 7,229,804. The *E. coli* strain generated a fermentation broth which had a P4HB titer of approximately 100-120 g of P4HB/kg of broth. After fermentation, the broth was washed with DI water by adding an equal volume of water, mixing for 2 minutes, centrifuging and decanting the water. Next, the washed broth was mixed with lime ($Ca(OH)_2$ standard hydrated lime 98%, Mississippi Lime) targeting 4% by wt dry solids. The mixture was then dried in a rotating drum dryer at 125-130° C. to a constant weight. Moisture levels in the dried biomass were approximately 1-2% by weight. The final wt % calcium ion in the dried broth+P4HB was measured by Ion Chromatography to be 1.9% (3.5% by wt. $Ca(OH)_2$).

Pyrolysis of the dried broth+P4HB+$Ca(OH)_2$ was carried out using a rotating, four inch diameter quartz glass kiln suspended within a clamshell tube furnace. At the start of the process, a weighed sample of dried broth+P4HB+$Ca(OH)_2$ was placed inside of the glass kiln and a nitrogen purge flow established. The furnace rotation and heat up would then be started. As the temperature of the furnace reached its set point value, gases generated by the broth+P4HB+$Ca(OH)_2$ sample would be swept out of the kiln by the nitrogen purge and enter a series of glass condensers or chilled traps. The condensers consisted of a vertical, cooled glass condenser tower with a condensate collection bulb located at the base. A glycol/water mixture held at 0° C. was circulated through all of the glass condensers. The cooled gases that exited the top of the first condenser were directed downward through a second condenser and through a second condensate collection bulb before being bubbled through a glass impinger filled with deionized water.

For the larger scale pyrolysis experiment, 292 g of dried broth+P4HB+$Ca(OH)_2$ was first loaded into the quartz kiln at room temperature. The total weight of P4HB biomass was estimated to be 281.4 g based on $Ca(OH)_2$ loading. The wt % P4HB in the mixture was also measured to be 66.7% based on the dry solids which made the mass of P4HB in the kiln equal to 195 g. The system was then sealed up and a nitrogen purge of approximately 1500 ml/min was established. Power was applied to the furnace and the dried broth+P4HB+$Ca(OH)_2$ was heated up to the target pyrolysis temperature of 250° C.

During pyrolysis, the products of the thermal degradation of biomass+P4HB, GBL, were collected in the condensate traps below the cooled condensers. Water could be seen to collect initially in each of the collection bulbs. The majority of the liquified product (>95%) was collected in the first glass collection bulb. Total pyrolysis run time was approximately 60 minutes. The weight of the remaining biomass after pyrolysis was measured to be 11.9 g.

After the completion of the pyrolysis run, the condensates from the condensers were collected and weighed. The results showed that the combined condensate weight was 181 g. Analysis of the condensate by Karl Fisher moisture analysis and GC-MS showed that the condensate contained 6.1% water, 0.06% fatty acids with the balance of the material being GBL products. The GBL product yield ((g of GBL product/g of starting P4HB)×100%) therefore was calculated to be approximately 87%. The GC-MS results also showed that the major impurity in the GBL product was GBL dimer where the peak area ratio of GBL/GBL dimer was calculated to be 2777. This was in agreement with the results from the experiment in Example 10 showing that the optimum process conditions for highest GBL purity were at the 250° C. pyrolysis temperature with the $Ca(OH)_2$ catalyst. Other impurities such as organosulfur and amide compounds were also detected as being present in the condensate by GC-MS. The conversion of the P4HB biomass solid to liquid ((g of dry Biomass−g Residual biomass/g of dry biomass)× 100%) was calculated to be 96%. GBL produced was tested for biobased content according to the standard ASTM-D6866-11 testing protocol and shown to have a biobased content of 99%.

Example 2. Post Purification of Biobased GBL by Distillation, Steam Stripping and Peroxide Treatment This example outlines a procedure for the purification of biobased GBL liquid prepared from pyrolysis of a genetically engineered microbe producing poly-4-hydroxybutyrate polymer mixed with a catalyst as outlined previously in Example 1.

The GBL purification is a batch process whereby the "crude" GBL liquid recovered after pyrolysis is first filtered to remove any solid particulates (typically <1% of the total crude GBL weight) and then distilled twice to remove compounds contributing to odor and color.

Filtration of the crude GBL liquid was carried out on a lab scale using a Buchner fritted-glass funnel coupled to an Erlenmeyer receiving flask. Approximately 1 liter of crude GBL was filtered which resulted in approximately 0.99 liters of recovered GBL liquid.

The distillation of the filtered GBL liquid was carried out using a high vacuum 20 stage glass distillation column. The stage section of the column was contained inside a silver-coated, evacuated, glass insulating sleeve in order to minimize any heat losses from the column during the distillation process. The distillation was performed under vacuum conditions using a vacuum pump equipped with a liquid nitrogen cold trap. Typical column operating pressures during distillation were in the 25 in. Hg range. Cooling water, maintained at 10° C., was run through the condenser at the top of the column to assist in the fractionation of the vapor. The column was also fitted with two thermocouples: one at the top of the column to monitor vapor temperature and one at the bottom of the column to monitor the liquid feed temperature. At the start of the distillation, approximately 1 liter of filtered GBL liquid was charged into the bottom of the column, the condenser cooling water and the vacuum were then turned on. Once the pressure had stabilized, the filtered GBL liquid was slowly heated using a heating mantle to the boiling point of GBL (204° C.).

During the initial stages of the distillation, water contained in the filtered GBL was removed first and discarded along with lower boiling impurities. When the water and lower boiling impurities were completely removed, the GBL liquid feed temperature increased to the boiling point of GBL. At this stage, the vapor generated at the top of the column was mostly GBL which was condensed, collected and reserved for further distillation. When it was observed that the temperature of the liquid feed increased quickly above 204° C., the distillation was stopped. The total amount of GBL liquid recovered in the first distillation was 0.9 liters with a purity of 97%.

After the remaining feed liquid from the first distillation was cooled, it was removed from the column and the 0.9 liters of distilled GBL liquid was added. Along with the distilled GBL liquid, 203 g (or 20% by weight GBL) of distilled/deionized water (MILLI-Q® Water System, Millipore) was added to the bottom of the column. The addition of the water was found to enhance removal of many impurities via steam stripping. After addition of the water, the second distillation was carried out under vacuum as described previously. The resulting GBL liquid recovered was shown to be 98% pure.

Another variation for the second distillation was tried whereby 1-3% (by weight GBL) of a 30% hydrogen peroxide solution was added along with the DI water to the previously distilled GBL liquid. The peroxide acts to oxidize the impurities in the GBL liquid making them less volatile and thereby easier to separate. To carry out this distillation, 0.9 liters of previously distilled GBL liquid were added to the bottom of the distillation column along with 203 g of DI water and 10.2 g of 30-32% hydrogen peroxide (Sigma Aldrich). The condenser cooling water and vacuum were started and the GBL liquid feed heated. The distillation generated a water fraction first and second transitional fraction prior to the pure GBL vapor. Both the first and second fractions were discarded and the pure GBL liquid collected. Analysis of the GBL liquid by GC-MS showed that is was >99.5% pure with very low odor and color. To remove additional water, the purified GBL liquid can be stored over dry molecular sieves (3-4 Å pore size, Sigma Aldrich) until used.

Another variation on the above purification steps is to add DI water and/or 30% hydrogen peroxide solution during the first distillation stage. Additional purification steps could include treatment with ozone, ion exchange resin or activated carbon.

Example 3. Production of Biobased-GBL from Purified P4HB Coupled with Thermolysis In this example biomass containing P4HB is produced in a fermentation process using glucose as the sole carbon feed source as described above. Following the fermentation, the P4HB is extracted from the biomass and purified. Suitable methods for purifying P4HB from biomass are described in for example U.S. Pat. No. 6,610,764 to Tepha and Metabolix and U.S. Pat. Nos. 7,981,642 and 7,576,173 to Metabolix Inc. Purified P4HB is subjected to a thermolysis procedure essentially under the same conditions as in Example 1 and GBL is produced. GBL produced using this approach should have a biobased content of around 99% when tested according to the standard ASTM-D6866-11 testing protocol.

Example 4. Production of Biobased-GHB from Purified P4HB Coupled with Catalyzed Depolymerization In this example, GHB is produced directly from purified biobased P4HB polymer by depolymerizing P4HB in an appropriate solvent. P4HB polymer is produced and purified as described in Example 3. The purified polymer is then dissolved in a solvent such as tetrahydrofuran (THF) and treated with 0.1.M sodium methoxide in methanol. Sufficient sodium methoxide is used to result in essentially complete degradation of the P4HB to the monomer GHB. The mixture is stirred at room temperature until the reaction is complete at which time the reaction mixture is quenched with acid essentially as described in U.S. Pat. No. 6,623,730. GHB produced using this approach should have a biobased content of around 99% when tested according to the standard ASTM-D6866-11 testing protocol.

Example 5. Production of Biobased P4HB Oligomers from Purified P4HB

In this example, GHB oligomers with different molecular weights, from 1,000 Daltons to 50,000 Daltons are produced directly from purified biobased P4HB polymer. Biobased P4HB polymer is first produced and purified as described in Example 3. The purified polymer is then dissolved in a solvent such as Tetrahydrofuran (THF) and treated with 0.1.M sodium methoxide in methanol. Sufficient sodium methoxide is used to result in degradation of the biobased P4Hb polymer to oligomers of the desired molecular weight. The mixture is stirred at room temperature until the reaction is complete at which time the reaction mixture is quenched with acid essentially as described in U.S. Pat. No. 6,623,730. P4HB oligomers produced using this approach should have a biobased content of around 99% when tested according to the standard ASTM-D6866-11 testing protocol.

Example 6. Production of Biobased GBL or GHB from Biobased Succinic Acid

The following example describes the production of GBL from biobased succinic acid via fermentation of microbial biomass, isolation of the succinic acid followed by catalytic hydrogenation. Several methods for producing succinic acid from renewable starting materials are described in the patent literature (U.S. Pat. Nos. 8,203,021 and 8,246,792; EP application 2,360,137; PCT application WO2010/092304). All of the patents describe the fermentation of a genetically modified microbial biomass (such as *E coli*) to produce a salt of succinic acid which is then isolated and purified to succinic acid using techniques well known in the art. The biobased content as measured by ASTM D6866 of the succinic acid produced by any of the methods should be at least 98%. To carry out the hydrogenation of the succinic acid, one can use the liquid phase procedure as described in U.S. Pat. No. 4,048,196 where a 50 mL autoclave is charged with 0.3 g of a Cu/Al/Zn oxide catalyst. The autoclave is then flushed with a 98%/2% nitrogen/hydrogen gas mixture and heated to 150° C. to reduce the catalyst. A 7% by weight solution of recovered biobased succinic acid product in DI water is then introduced into the reactor to a total weight of 10 g. The reactor is further pressurized to 250 bar with pure $H_2$ gas and the hydrogenation reaction is allowed to proceed for 1-2 hours. Upon completion of the reaction, the reactor is cooled and de-pressurized followed by flushing with nitrogen. The autoclave contents are discharged and the catalyst separated by decantation. The catalyst is washed with additional DI water and the wash is added to the supernatant. An aliquot of supernatant is filtered and analyzed by HPLC to determine the percent conversion of succinic acid and the percent yield of GBL on a molar basis. Alternatively, one could use a vapor phase, catalytic hydrogenation procedure as described in EP 1,047,687 to convert the succinic acid to GHB or GBL.

Example 7. Production of Biobased GBL or GHB from Biobased 1,4-Butanediol

The following example describes the production of GBL from biobased 1,4-butanediol (BDO) via fermentation of microbial biomass, isolation of the BDO followed by catalytic oxygenation. Several methods for producing 1,4-butanediol from renewable starting materials are described in the patent literature (US patent applications 2009/0075351 and 2010/00304453). The patents describe the use of a genetically-modified biomass (such as *E. coli*, yeast etc.) to produce BDO from starting materials such as glucose, methanol, syngas (a CO, $CO_2$, $H_2$ mixture), α-ketoglutarate or succinate. The BDO produced by culturing the genetically-modified microorganisms is then isolated and purified using techniques well known in the art. The biobased content as measured by ASTM D6866 of the purified BDO produced by the above method should be at least 98%. In order to convert the biobased 1,4-butanediol to GBL a catalytic oxidation is carried out. The BDO is first heated to 25° C. and is then fed with a pump through a liquid rotameter to the top of an electrically heated vaporizer where it is contacted with air fed through a separate rotameter to the bottom of the vaporizer. The vaporizer is operated at 150° C. to 200° C. and filled with stainless steel wool to ensure good heat transfer and efficient vaporization and mixing of crotonic acid and air. The mixture is then sent to an electrically heated preheater, also filled with stainless steel wool, and heated to 250° C. to 300° C. The vapor stream is sent to a fixed catalyst bed consisting of ⅛ alumina granules impregnated with vanadium pentoxide (as described in more detail in Church, J. M. and Bitha, P., "Catalytic air oxidation of crotonaldehyde to maleic anhydride", I&EC Product Research and Development, Vol. 2 (1), 1963, p 61-66) contained within a jacketed reactor vessel. The reactor is heated electrically for start-up and cooled using circulating heat transfer oil to maintain reactor conditions. The exit gases are fed to a water cooled cyclone separator to allow the maleic anhydride and crotonic acid to condense. Any uncondensed product and still present in the light gases are then absorbed in a packed tower with circulating cold water used as direct contact scrubbing liquid. At the end of the run the liquid product from the cyclone separator and scrubbing liquid are collected and analyzed to calculate GBL yield (as percentage of theoretical) and conversion of BDO.

Example 8. Production of Biobased Sodium-GHB from Biobased GBL

In this example, any of the biobased GBL produced in the preceding examples are used as the starting material to produce the sodium salt of gamma-hydroxybutyrate which is a pharmaceutical compound currently used to treat such medical conditions as narcolepsy and cataplexy. Biobased GBL (24.4 mol) is slowly added to a solution of NaOH (25 mol in 2 L of water and 400 ml of ethanol) with mechanical stirring and the reaction allowed to warm to reflux for 1 hour. Ethanol is removed by distillation resulting an aqueous solution containing 70% sodium GHB by weight. GHB produced using this approach should have a biobased content of around 99% when tested according to the standard ASTM-D6866-11 testing protocol. By combining biobased GBL with petroleum based GBL in a ratio of 5:95 GHB having from approximately 5-95% biobased content can be produced using the procedure described in this example.

Example 9. Production of a Pharmaceutical Composition Containing Biobased Sodium-Gamma-Hydroxybutyrate (Na-GHB)

In this example, a method for preparing a microbially stable, biobased Na-GHB (as produced in Ex. 8) pharmaceutical formulation is described (see U.S. Pat. No. 8,263,650). To prepare a microbially stable pharmaceutical formulation, Na-GHB is dissolved in DI water to a concentration of about 500 mg/ml. The pH is adjusted with malic acid, HCl, citric acid or other acids to a value from 7.3-8.5. These acids also act as buffers to maintain the pH within the optimum range to prevent conversion of the GHB to GBL and to prevent microbial growth during storage.

Example 10. Continuous Production of a Pharmaceutical Composition Containing Biobased GHB Biobased GBL produced as described in the above examples can be used in a continuous process to produce GHB for pharmaceutical applications as described in PCT WO2012051473 to Norac Pharma.

Example 11. Compositions Containing Biobased GHB Moieties for Enhancing Treatment of Patients Biobased GBL or GHB is used for making enhanced compositions comprising GHB moieties for treating patients essentially as described in U.S. Pat. No. 7,572,605B2.

Example 12. Compositions Containing Biobased Deuterated Na-GHB

Biobased Na-GHB having one or more hydrogen atoms replaced with deuterium atoms can be prepared by starting with biobased GBL as prepared in Examples 1-7 and following the procedure described in Patent Application No. US2012/0122952 assigned to Concert Pharmaceuticals. Biobased GBL is first converted to the butyl ester by reaction with butanol using an acid catalyst. The t-butyl ester of GBL is then reacted in deuterated methanol in the presence of potassium carbonate to effect a hydrogen-deuterium atom exchange. After the hydrogen-deuterium exchange is complete, the compound is saponified with sodium hydroxide to form a biobased deuterated sodium oxybate. Alternatively, one could use deuterated feedstocks (sugar, acetic acid or $D_2O$) to make the starting succinic acid, 1,4-butanediol or GBL materials which are then converted to Na-GHB as described in the previous examples.

Example 13. Compositions Containing Biobased Fluorinated Na-GHB

International Patent Application No. WO2102/142162 outlines a method and materials for fluorinating hydroxyl organic compounds such as pharmaceutical intermediates or precursors. The method can be applied to biobased sodium oxybate as prepared in Example 8.

Example 14. Generation of Immediate Release, Biobased Sodium Oxybate Solid Dosage Formulation U.S. Patent Application Publication No. US20110111027 assigned to Jazz Pharmaceuticals describes a solid dosage form containing sodium oxybate which when taken orally is capable of quickly releasing 90% of the gamma-hydroxybutyrate active pharmaceutical in less than 1 hour similar to the effect when administering liquid sodium oxybate. The formulation contains Na-GHB (70-90% by weight), a binder e.g. hydroxypropyl cellulose (1-10% by weight), a lubricant e.g. magnesium stearate (0.5-5% by weight) and a surfactant e.g. sodium lauryl sulfate (0.5-3% by weight). The ingredients can be combined either in a dry or wet granulation procedure and then pressed into a tablet. In the wet procedure ethanol was used to first dissolve the hydroxypropyl cellulose binder. Similar formulations could also be made by substituting biobased sodium oxybate as prepared in Example 8 into the immediate release formulation as described above to form a biobased, immediate release, sodium oxybate solid dosage tablet.

Example 15. Controlled Release Solid Dosage Forms of Biobased Ultra High Purity Sodium Oxybate U.S. Patent Application Publication No. US20120076865 assigned to Jazz Pharmaceuticals describes controlled release dosage forms for water soluble and hygroscopic drugs such as sodium oxybate. The formulation as describes includes both an immediate release coating of sodium oxybate and a controlled released solid core of sodium oxybate. The core is composed of Na-GHB (90-100% by weight) and a polymer binder such as hydroxypropylene cellulose or ethyl cellulose (1-10% by weight) that are used for preparing the solid tablets. Other components may be added to the controlled release core such as lubricants, surfactants, plasticizers, excipients, compression aids or other fillers.

The core is formed by wet granulation, roller compaction or direct compression. Once the core is formed, it is then coated to facilitate the controlled release of the sodium oxybate in the GI tract as well as to retain the integrity of the unit dosage form. The coating is a blend of a polymer e.g. cellulose polymers (50-80% by weight), a pore former which modifies the permeability of the coating e.g. hydroxypropyl cellulose, sugars or organic acids and other fillers or additives. It is applied to the core at about 2.5-7.5% by weight of the total tablet weight. The thickness of the coating also imparts control of the rate of release of the sodium oxybate from the core and can be varied to modulate the delivery of the pharmaceutical. The release profile sodium oxybate from the coated tablet was shown to be in the range of 6-8 hours or more.

Prior to administering the coated tablet, it can also be coated with an immediate release film containing sodium oxybate as described in Example 14. In this way the tablet delivers a predetermined concentration of sodium oxybate within the first hour then maintains a sustained release profile over the next 6-8 hours. Similar controlled release formulations could be made by substituting the ultra high purity, biobased sodium oxybate prepared in Example 8 into the formulation as described above. Thereby making a biobased, controlled release, sodium oxybate solid dosage tablet.

Example 16. Synthesis of Deuterated P4HB Using $D_2O$ or Deuterated Glucose as the Deuterium Source Deuterium oxide ($D_2O$) and glucose-1,2,3,4,5,6,6-d7 were purchased from Sigma Aldrich. Two solutions of minimal salts media (MSM) were prepared. One solution used $D_2O$ as the source for all water components, except for a small addition of trace salts solution which added a 1:1000 $H_2O$ component to the deuterated solution. The second solution contained only $H_2O$. In addition, a deuterated LB medium and 500 g/L glucose solution in $D_2O$ were used.

The homopolymer P4HB strain MBX4743 was chosen for this experiment. MBX4743 was inoculated into LB $H_2O$ medium from a glycerol stock, and incubated overnight at 250 RPM and 37° C. One mL of the overnight culture was subcultured into 2 mL of both LB-$D_2O$ and LB-$H_2O$, and incubated in the shaker for 2 hours at 37° C. The LB-$D_2O$ overnight culture was used to subculture into $D_2O$ minimal salts media, while the LB-$H_2O$ culture was used to subculture into $H_2O$ minimal salts media. All subcultures were incubated in the shaker for 3 hours at 37° C. (FIG. 1). The $H_2O$-MSM culture was used to inoculate the control (Table 1, condition 1), while the $D_2O$-MSM culture was used to inoculate all other conditions (Table 1).

TABLE 1

Fermentation medium conditions

| Condition Number | Medium | Glucose Fed (mg) |
|---|---|---|
| 1 | 100% $H_2O$, MSM | 756 unlabeled glucose |
| 2 | 50% $D_2O$ + 50% $H_2O$, MSM | 689 unlabeled glucose |
| 3 | 75% $D_2O$ + 25% $H_2O$, MSM | 376 unlabeled glucose |
| 4 | 100% $D_2O$, MSM | 220 unlabeled glucose |
| 5 | 25% $D_2O$ + 75% $H_2O$, MSM | 49 heavy glucose + 69 unlabeled glucose |
| 6 | 50% $D_2O$ + 50% $H_2O$, MSM | 378 heavy glucose |
| 7 | 100% $D_2O$, MSM | 200 heavy glucose |

Seven fermentation medium conditions with different amounts of $D_2O$ and labeled glucose were prepared (Table 1). Four hundred μL of MSM cultures were used to inoculate 24 wells in the MICRO24 reactor (Table 2). The pH was kept at 6.9 via an $NH_4OH$ bubbler and the dissolved oxygen (DO) was maintained at 20% via a pure oxygen feed. The fermentation was allowed to proceed for 42 hours. Glucose feeding occurred at the discretion of the operator with an attempt to maintain the glucose concentration at 30 g/L. Unlabeled 500 g/L glucose in $H_2O$ was used to feed the control (condition 1). Unlabeled 500 g/L glucose in $D_2O$ was used to feed conditions 2, 3, 4, and 7. Different amounts of labeled 500 g/L glucose-1, 2, 3, 4, 5, 6, 6-d7 ("heavy glucose") in $D_2O$ were used in the conditions 5 through 7.

TABLE 2

The conditions of each well in the 24 wells of the MICRO24 cassette. The numbers in each cell correspond to the fermentation medium conditions in Table 1 (1 through 7).

| | Column | | | | | |
|---|---|---|---|---|---|---|
| Row | C-1 | C-2 | C-3 | C-4 | C-5 | C-6 |
| A | 1 | 1 | 4 | 4 | 4 | 5 |
| B | 1 | 1 | 4 | 4 | 7 | 6 |
| C | 1 | 1 | 3 | 3 | 3 | 3 |
| D | 1 | 1 | 2 | 2 | 2 | 2 |

Wells containing the same condition were pooled together. A sample of broth from each condition was centrifuged down, washed with $H_2O$, freeze dried, and converted to the butyl-ester form through butanolysis. The remaining broth from each condition was used for polymer extraction and purification for $^1$H-NMR analysis.

Results

After 42 hours of fermentation in the MICRO24, all conditions with the exception of condition 7 reached high cell density with greater than 50% P4HB accumulation (Table 3).

TABLE 3

Cell growth in the MICRO24

| Condition Number | Medium | Glucose Fed (mg) | Final Biomass Titer (g/L) |
|---|---|---|---|
| 1 | 100% $H_2O$, MSM | 756 unlabeled glucose | 32.6 |
| 2 | 50% $D_2O$ + 50% $H_2O$, MSM | 689 unlabeled glucose | 26.9 |
| 3 | 75% $D_2O$ + 25% $H_2O$, MSM | 376 unlabeled glucose | 23.8 |
| 4 | 100% $D_2O$, MSM | 220 unlabeled glucose | 3.5 |
| 5 | 25% $D_2O$ + 75% $H_2O$, MSM | 49 heavy glucose + 69 unlabeled glucose | 13.1 |
| 6 | 50% $D_2O$ + 50% $H_2O$, MSM | 378 heavy glucose | 13.6 |
| 7 | 100% $D_2O$, MSM | 200 heavy glucose | No growth |

The fermentation samples were analyzed via GC-MS for isotopomer distribution. A typical GC chromatogram of P4HB shows two dominant peaks due to P4HB: butyl-4-chlorobutyrate at 7.68 min and butyl-4-butoxybutyrate at 10.18 min. Either of the two peaks could be used to determine the molecular weight distribution of 4HB, the monomer repeat unit of P4HB. The peak that correlated with butyl-4-butoxybutyrate was chosen for further analysis. A typical fragmentation pattern of butyl-4-butoxybutyrate shows the base ion at m/z 87 and the parent ion at m/z 159. Both patterns can be used to determine the isotopomer distribution but the parent pattern at m/z 159 was chosen for further analysis for simplicity.

Results of GC-MS at m/z 159 for the six conditions are summarized in Table 4.

TABLE 4

GC-MS results. The m/z of 159 corresponds to the parent ion without any deuterium. The m/z of 165 corresponds to the ion with six deuteriums. The data were corrected for the presence of naturally occurring $^{13}C$ (1.07%) from the glucose in the fermentation medium and the butanol in the butanolysis reaction. The contribution due to the natural abundance of deuterium (0.0115%) is small and thus neglected.

| Condition Number | m/z | | | | | | | | Number of deuterium at 4HB | Percent of deuteration at 4HB |
|---|---|---|---|---|---|---|---|---|---|---|
| | 159 (0 D) | 160 (1 D) | 161 (2 D) | 162 (3 D) | 163 (4 D) | 164 (5 D) | 165 (6 D) | 166 | | |
| 1 | 97% | 0% | 3% | | | | | | | |
| 2 | 4% | 18% | 30% | 28% | 15% | 4% | 1% | | 2.47 | 41% |
| 3 | 1% | 4% | 16% | 30% | 30% | 16% | 4% | | 3.46 | 58% |
| 4 | 2% | 0% | 1% | 7% | 24% | 41% | 24% | 1% | 4.79 | 80% |
| 5 | 19% | 28% | 31% | 16% | 5% | 1% | | | 1.63 | 27% |
| 6 | 2% | 2% | 9% | 23% | 32% | 24% | 8% | 1% | 3.90 | 65% |

Since 4HB in the polymer form has six hydrogen atoms, seven molecular weight species are theoretically possible depending on the number of hydrogen atoms that are substituted with deuterium (from zero (m/z of 159) to six deuteriums (m/z of 165)).

The GC-MS results indicated that the extent of deuterium incorporation into P4HB varied, depending on the fermentation conditions that were used. The results of conditions 2 through 5, in which $D_2O$ was the only source of deuterium, demonstrated that deuterium can be incorporated into P4HB using $D_2O$ as the deuteration source. In addition, the extent of incorporation varied with the amount of $D_2O$ that was added to the medium. The use of deuterated glucose also increased the degree of deuteration (conditions 6 and 7).

When 100% $D_2O$ was used (condition 5), the most abundant 4HB species obtained was the five-deuterium (5D) species with 41% abundance. 4HB labeled with six deuterium atoms (6D) could also be obtained (24% abundance). The average number of deuterium atoms that could be incorporated using 100% $D_2O$ was 4.79 substitutions per 4HB monomer unit, resulting in 80% deuteration.

The samples of conditions 1 and 5 were analyzed via $^1$H-NMR to independently confirm the deuteration results of GC-MS. The multiplet patterns of the peaks at the C-2, C-3, and C-4 positions of P4HB confirmed the incorporation of deuterium into P4HB. The C-4 peak at 4.109 ppm shows a triplet with the intensity of 1:2:1, the C-3 peak at 1.955 ppm shows a quintet with the intensity of 1:4:6:4:1, and the C-2 peak at 2.383 ppm shows a triplet with the intensity of 1:2:1.

The $^1$H-NMR spectrum of condition 5 shows a different pattern because the incorporation of deuterium changes the multiplet pattern: the C-4 peak shows a doublet indicating that at least one of the hydrogen atoms at the C-3 position are replaced with deuterium. The C-3 peak is a doublet indicating that most of the hydrogen atoms at the C-2 and C-4 positions are replaced with deuterium (three of the four coupled atoms at the C-2 and C-4 positions are substituted). The C-2 peak is also a doublet indicating that at least one of the hydrogen atoms at C-3 are replaced with deuterium.

The $^1$H-NMR spectrum of condition 5 is qualitatively consistent with the distribution of the molecular weight species as determined by GC-MS: the D5 species and D6 species would not produce any peaks in $^1$H-NMR. The most abundant species with the abundance of 41% was D4 species which contains only two hydrogen atoms. There are six isotopomers of the D4 species. Each of the six isotopomers has a different proton splitting pattern. The peak at each carbon position is a superposition of the peaks from the six isotopomers.

Since there exist only a doublet and a singlet due to the D4 species, the peak at each position can be a three-peak multiplet, as opposed to a triplet which differs in intensity pattern and chemical shift. Alternatively, a singlet or a doublet will dominate at each position if any of the isotopomers is the most dominant. The doublet pattern was dominant at all the three carbon positions indicating that isotopomers 1 and 4 were probably the most dominant.

We claim:

1. A method for producing a sample from an approved source, said method comprising:

fermenting engineered microbes which produce poly(4-hydroxybutyrate) (P4HB) polymer with a growth medium comprising $D_2O$ with deuterated glucose or without deuterated glucose to produce a deuterated P4HB;

reacting the deuterated P4HB for obtaining a deuterated gamma-butyrolactone, a deuterated 4-hydroxybutyrate, an oligomer of deuterated 4-hydroxybutyrate, or a combination thereof; and mixing the reacted deuterated P4HB with a gamma-butyrolactone prepared from petroleum-based starting materials, a 4-hydroxybutyrate prepared from petroleum-based starting materials, an oligomer of 4-hydroxybutyrate prepared from petroleum-based starting materials, or a combination thereof to prepare a mixture of GBL, a mixture of GHB, a mixture of oligomers of 4-hydroxybutyrate, or a mixture comprising a combination thereof, wherein the mixture has a chosen percent modern carbon range, wherein the growth medium comprises a selected mixture of a biobased material and a petroleum-based material to yield a desired percent modern carbon, wherein a percentage of the carbon in the deuterated P4HB is modern carbon and the remaining percentage of carbon is fossil-carbon, wherein the chosen percent modern carbon range is controlled to provide a unique carbon footprint, and wherein the chosen percent modern carbon range corresponds to a defined range of the approved source, wherein the growth medium comprises a concentration of $D_2O$ above the natural abundance in water, and wherein the deuterated P4HB produced by fermenting is 27% to 80% deuterated.

2. The method of claim 1, wherein the percentage of the carbon in the deuterated P4HB that is modern carbon is at least 80% as measured by the ASTM D6866 protocol.

3. The method of claim 1, wherein the reacting comprises pyrolysing the deuterated P4HB under the condition suitable for pyrolysis of the deuterated P4HB.

4. The method of claim 1, wherein the reacting comprises reacting the deuterated P4HB with a base under the condition suitable for base-catalyzed hydrolysis of the deuterated P4HB.

5. The method of claim 1, wherein the reacting comprises reacting the deuterated P4HB with a base in the presence of a catalyst under the condition suitable for a catalyzed depolymerization of the deuterated P4HB.

6. The method of claim 1, wherein the growth medium comprises $D_2O$ without deuterated glucose and wherein the $D_2O$ is the only deuterium source above natural abundance in the growth medium.

\* \* \* \* \*